US 6,620,788 B1

(12) United States Patent
Tanida et al.

(10) Patent No.: US 6,620,788 B1
(45) Date of Patent: Sep. 16, 2003

(54) ENTERAL SORBEFACIENTS

(75) Inventors: Norifumi Tanida, Ryuugasaki (JP); Takeshi Goto, Ryuugasaki (JP); Satoshi Suzuki, Tosu (JP)

(73) Assignee: Hisamitsu Pharmaceutical Co., Inc., Ibarki (JP)

( * ) Notice: Subject to any disclaimer, the term of this patent is extended or adjusted under 35 U.S.C. 154(b) by 0 days.

(21) Appl. No.: 09/913,761

(22) PCT Filed: Feb. 25, 2000

(86) PCT No.: PCT/JP00/01090

§ 371 (c)(1),
(2), (4) Date: Jan. 7, 2002

(87) PCT Pub. No.: WO00/50083

PCT Pub. Date: Aug. 31, 2000

(30) Foreign Application Priority Data

Feb. 26, 1999 (JP) ............................................. 11-050970

(51) Int. Cl.$^7$ ............................ A61K 38/00; A61K 9/48
(52) U.S. Cl. ......................................... 514/12; 424/463
(58) Field of Search .............................. 514/12; 424/463

(56) References Cited

U.S. PATENT DOCUMENTS

| 4,476,116 | A |   | 10/1984 | Anik ............................ 424/177 |
| 4,882,359 | A |   | 11/1989 | Nakagawa et al. .......... 514/947 |
| 5,171,580 | A |   | 12/1992 | Iamartino et al. ............ 424/490 |
| 5,578,567 | A |   | 11/1996 | Cardinaux et al. ............. 514/12 |
| 5,654,004 | A |   | 8/1997  | Okayama et al. ............ 424/479 |
| 5,674,874 | A |   | 10/1997 | Hausheer et al. .............. 514/283 |
| 6,214,378 | B1 | * | 4/2001 | Tanida et al. ................ 424/463 |

FOREIGN PATENT DOCUMENTS

| EP | 0 049 590 A2 | 9/1981 |
| EP | 0 115 627 A1 | 12/1983 |
| EP | 0 225 189 A2 | 11/1986 |
| EP | 0 610 502 A1 | 9/1992 |
| EP | 0 754 452 A2 | 1/1997 |
| EP | 0 919 288 A1 | 6/1999 |
| JP | 59-130820 | 7/1984 |
| JP | 2-42027 | 2/1990 |
| JP | WO 90/13286 | 11/1990 |
| JP | 4-247034 | 9/1992 |
| JP | 4-501411 | 12/1992 |
| JP | WO 94/10983 | 5/1994 |
| JP | 6-43390 | 8/1994 |
| JP | WO 95/28963 | 2/1995 |
| JP | 9-87169 | 3/1997 |
| JP | 10-152431 | 9/1998 |
| WO | WO 83/00435 | 2/1983 |

\* cited by examiner

Primary Examiner—Kevin E. Weddington
(74) Attorney, Agent, or Firm—Licata & Tyrrell P.C.

(57) ABSTRACT

An absorption enhancer for the large intestine most suitable for an oral preparation, with a disintegration property in the large intestine, especially the absorption enhancer for the large intestine mixed with a hydrophilic medium and an absorption enhancer is provided.

13 Claims, 1 Drawing Sheet

ENTERAL SORBEFACIENTS

TECHNICAL FIELD OF THE INVENTION

The invention relates to an absorption enhancer for the large intestine.

BACKGROUND ART

Physiologically active polypeptides or oligonucleotides have hitherto been developed as a preparation for an intravenous, intranasal or rectal administration. However, owing to the inconvenience in using these administration forms, the dosage form is most desired to be an oral administration form.

In order to formulate a physiologically active polypeptide or an oligonucleotide into a dosage form for oral administration, first it is necessary that the polypeptide or oligonucleotide is not degraded in the digestive tract. For this reason, it is important to target a site in which the degradation activity for these physiologically active substances is as low as possible.

On the other hand, owing to the fact that the large intestine has extremely low protease activity and that drug absorption is greatly improved by addition of an absorption enhancer, it has been better recognized as a new site for drug administration. However, conventional oral preparations are not necessarily satisfactory in that they disintegrate and dissolve before the arrival at the large intestine, resulting that a physiologically active polypeptide or oligonucleotide which is administered orally is easily degraded by a hydrolytic enzyme in the small intestine. Therefore, development of a delivery technology for the large intestine has to date been tried from several different angles.

For example, there have been reported an oral preparation targeting the large intestine, which is prepared by combining a polymer soluble only at the pH of 5.5 or above and an insoluble polymer (EP, 49590, A); a solid oral preparation coated with a suitable amount of an anionic polymer soluble at the pH of 7.0 or above (trade name: Eudragit S, a product of Röhm GmbH) (WO83/00435); an oral preparation coated with an anionic polymer soluble at the pH of 7.0 or above (trade name: Eudragit S, a product of Röhm GmbH) and a methacrylate copolymer poorly water soluble (trade name: Eudragit RS, a product of Röhm GmbH) at a suitable composition rate (EP, 225189, A); an osmotic-pump preparation coated with an enteric polymer; an oral pharmaceutical preparation reaching the large intestine, which is covered with an inner coat soluble at the pH of 7.0 or above, an intermediate coat made of a gelatinized polymer, and a stomach-proof outer coat soluble at the pH of 5.5 or above (JP, 4-501411, A); and so forth. Further, several delivery technologies using a coating polymer for a pharmaceutical additive have been reported (WO 90/13286; JP, 9-87169, A; WO 95/28963).

The inventors of the present invention have also proposed an oral preparation of releasing at lower intestinal tracts, having a high specificity to the large intestine (WO 94/10983; JP, 10-152431, A). This preparation is characterized in that it consists of double-coating structure in which the case of tablets compressively molded, granules, or capsules filled with powder of a liquid preparation is coated with an inner layer consisting of a cationic copolymer and an outer layer consisting of an anionic copolymer. This preparation has a very good specificity to the large intestine and enabled to release a drug targeted to the large intestine in a more reliable and rapid way.

The development of these delivery technologies targeting the large intestine makes it possible to deliver a peptide drug or a nucleotide drug in an unchanged state and to utilize the large intestine as a new absorption site, though a satisfactory absorption efficiency is not necessarily obtained in a polymer drug like peptides. It is considered that this comes from the reason that, owing to a tight cell function in a large-intestinal part, the absorption of a highly hydrophilic polymer peptide drug is usually difficult.

Thus, modifications to obtain better absorption from a large-intestinal mucous membrane have also been tried. One of them is a method to use an absorption enhancer which is widely used to facilitate a transmucosal absorption in preparation such as an intranasal, intravaginal, rectal or oral preparation. As for an absorption enhancer, mainly reported are bile acid salts having a surfactant action (JP, 59-130820, A), ionic or non-ionic surfactants (JP, 4-247034, A), chelating agents, medium chain fatty acid salts (U.S. Pat. No. 4,476,116, A), alkali metal glycyrrhinates (JP, 2-42027, A), azacycloalkane derivatives (JP, 6-43390, B) and the like.

However, the present situation is that an absorption enhancer for a transmucosal developed so far is yet to be fully used for the large intestine compared with the intranasal and other transmucosal use. As the reason for this, it is pointed out that, first, in case of the administration in a solution state conventional absorption enhancers are mostly rapid in the absorption and are not enough in durability. Further, even if in the case that durability of an absorption-promoting action is strong, in the state of an aqueous solution, the administration can only be made in a method like intraintestinal one, being inferior in usability. On the other hand, in the case that one in a powder state is applied to an oral preparation with a disintegration property in the large-intestinal environment, solubility of a drug or an absorption enhancer is not enough due to the insufficiency of the amount of water in the large intestine. These become reasons that other mucous membrane absorption enhancers can not easily be applied to the large-intestinal use.

Thus, although the large intestine is noted as a preferable absorption site in a digestive tract for physiologically active polypeptides or oligonucleotides, a fully satisfactory preparation technology has not yet been developed.

The object of the invention therefore is to provide an absorption enhancer for the large intestine, having a highly absorption enhancer effect to solve the above problems, especially an absorption enhancer for the large intestine suitable for an oral preparation having a disintegration property in the large intestine.

Disclosure of the Invention

The inventors, by conducting extensive researches to solve the above problems, found out that they can be solved by mixing a hydrophilic medium with an absorption enhancer and completed the invention.

The invention is based on a finding, through a screening of existing absorption enhancers by rat in situ loop experiments for evaluating the absorption of a drug in the rat large intestine, that the absorption enhancer effect is increased by mixing absorption enhancers such as azacycloalkane derivatives, medium-chain fatty acids or bile acids with a hydrophilic medium such as polyethylene glycol or glycerin, which alone do not show any absorption-promoting effect. Further, the invention is based on a finding that owing to the achieved preparation in a state wherein a poorly water soluble absorption enhancer is dissolved by a hydrophilic medium, which can strongly absorb water in a large-intestine tract, a water-soluble peptide type drug can rapidly be eluted from the preparation.

Namely, the invention relates to an absorption enhancer for the large intestine containing a hydrophilic medium and an absorption enhancer.

Also, the invention relates to the absorption enhancer for the large intestine wherein the hydrophilic medium is polyethylene glycol with the average molecular weight in the range of 190 to 630 or glycerin.

The invention also relates to the absorption enhancer for the large intestine wherein the absorption enhancer is one or more types selected from the group consisting of azacycloalkane derivatives, bile acid salts and medium-chain fatty acid salts.

Further, the invention also relates to the absorption enhancer for the large intestine wherein the azacycloalkane derivative is 1-[2-(decylthio)ethyl]azacyclopentan-2-one.

Also, the invention relates to the absorption enhancer for the large intestine wherein the bile acid salt is one or more types selected from the group consisting of sodium cholate, sodium glycocholate, sodium taurocholate, sodium deoxycholate and sodium chenodeoxycholate.

The invention also relates to the absorption enhancer for the large intestine wherein the medium-chain fatty acid salt is one or more types selected from alkaline metal salts of capric acid, caprylic acid or caproic acid.

Further, the invention relates to an oral preparation containing the above absorption enhancer for the large intestine.

Furthermore, the invention relates to an oral preparation wherein the physiologically active polypeptide or oligonucleotide is contained as an active ingredient.

Mode for Carrying out the Invention

Figure 1:
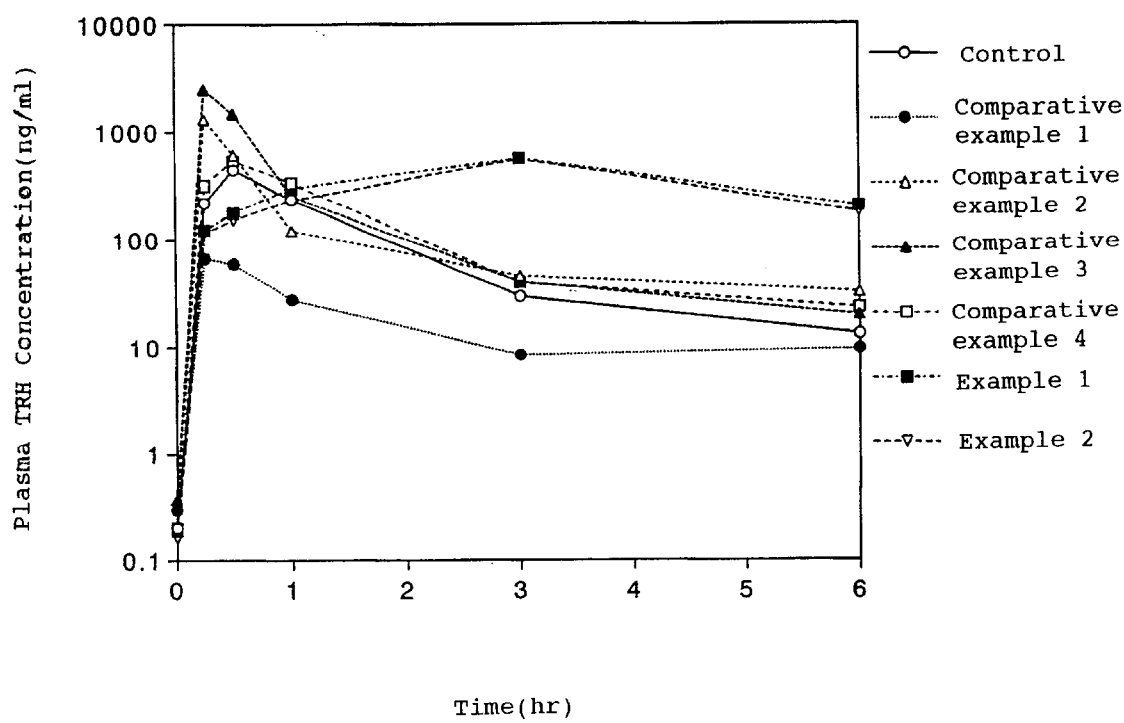
FIG. 1 is a graph showing the plasma concentration change of TRH-T (protirelin tartarate) in each formulation solution in case of using the prepared absorption enhancer solution and evaluating the effect of each absorption enhancer by a rat in situ loop experiment.

In the following, the embodiment of the absorption enhancer for the large intestine in accordance with the invention is illustrated in more detail.

In the absorption enhancer for the large intestine in the invention, as a hydrophilic medium used are polyethylene glycols, glycerin or the like. As a utilizable hydrophilic medium, one having preferable physicochemical properties is appropriately selected in consideration of decrease of solubility and dispersiveness of the main pharmaceutical ingredient from the preparation in the body. For example, polyethylene glycols, preferably with the average molecular weight of 190 to 630, especially preferably with the average molecular weight range of 285 to 630 are used. Further, those with freezing point of 25° C. or lower, that is, those which are not in a solid state at room temperature, is preferable, and those having the range of −15° C. to 25° C. are especially preferable. Furthermore, those having a preferable relative hygroscopicity are selected in consideration of the water utilization rate in a large-intestinal tract, dissolution and dispersion of the main pharmaceutical ingredient, separation of an oil type absorption enhancer from abase, and the like, though a hydrophilic medium with the relative hygrous degree of 40 to 100, especially polyethylene glycol with 40 to 70 is preferable (assuming the hygrous degree of glycerin is 100). The mixing amount of these hydrophilic media in the total amount of the preparation is determined in consideration of the water utilization rate in a large-intestinal tract, dissolution and dispersion of the main pharmaceutical ingredient, the absorption rate of the pharmacologically active substance, and the like, though they are used in the range of 30 to 93%, preferably 50 to 90%, more preferably 60 to 80%.

Illustrative of the absorption enhancers are azacycloalkane derivatives, bile acid salts or medium-chain fatty acid salts.

First, illustrative of the azacycloalkane derivatives are compounds described in (JP, 6-43390, B) among which especially 1-[2-(decylthio)ethyl]azacyclopentan-2-one (hereinafter referred to as pirotiodecane) is preferable.

Illustrative of the medium-chain fatty acids or salts thereof are preferably capric acid, caprylic acid, caproic acid or the like, or salts thereof.

Illustrative of the bile acids or salts thereof are preferably cholic acid, glycocholic acid, taurocholic acid, deoxycholic acid, chenodeoxycholic acid or salts thereof.

The mixed amount of these absorption enhancers in the total amount of a preparation is determined in consideration of the water utilization rate of the preparation, dissolution and dispersion of the pharmacologically active substance, the absorption enhancer effect and the like, though that in the range of 5 to 50%, preferably 10 to 40%, more preferably 20 to 30% is used.

In the invention the mixing ratio between the absorption enhancer and the hydrophilic medium is preferably 1:1 to 1:100.

Also, the mixing proportion of pharmacologically active substances shown below is determined by consideration of a type, though it is typically used in the range of 1 to 50%.

This absorption enhancer for the large intestine is prepared into an oral preparation by mixing a pharmacologically active substance.

There is no particular limitation for the pharmacologically active substance if it is an active substance when absorbed from a mucous membrane of the large intestine. Examples include peptide drugs and protein drugs such as somatostatin, insulin, angiotensin, gastrin, pentagastrin, glucagon, calcitonin, CGRP (calcitonin gene-related peptide), EGF (epidermal growth factor), α-ANP (α-human atrial naturiuretic peptide), GM-CSF (granulocyte-macrophage colony stimulating factor), G-CSF (granulocyte colony stimulating factor), t-PA (tissue plasminogen activator), TNF (tumor necrosis factor), TCGF (T cell growth factor), hCF (human growth hormone), ACTH (adrenocorticotropic hormone), MSH (melanocyte stimulating hormone), LH (luteinizing hormone), LHRH (luteinizing hormone releasing hormone), enkephalin, endorphin, muramyl dipeptide, neurotensin, interleukins, interferon, EPO (erythtopoietin), urokinase, neocarcinostatin, oxytocin, thyroid hormone, TRH (thyrotropin-releasing hormone), PTH (parathyroid hormone), desmopressin, vasopressin, vasoactive intestinal peptide, cholecystokinin, bradykinin, immunoglobulin and its digested products or its derivative, various allergens and their digested products or their derivatives, and the like.

Further, gene relating drugs herein utilizable include DNAs, RNAs, and their modified compounds, and their conjugated or bound compounds to a carrier, nucleic acids, oligonucleotides, antisense oligonucleotides, triple helix forming olignucleotides (TFO), ribozymes, decoys, plasmids and the like. Illustrative of the carriers used are cationic polymers, cationic lipids, virus vectors, phages, and the like. Specifically, illustrative of these are suppressive type gene pharmaceuticals such as TNF-α, ICAM-1, COX-2, IL-1, IL-6, HIV (human immunodeficiency virus), bile acid transporter and each transporter of the small intestine, or expression type gene pharmaceuticals such as INF-γ, TNF-α, G-CSF (granulocyte colony-stimulating facor), GM-CSF (granulocyte macrophage colony-stimulating facor), glucose transporter, LHRH (luteonizing hormone-releasing hormone) and calcitonin.

The absorption enhancer for the large intestine in the invention can be prepared into a preparation by mixing the above pharmacologically active substance together with a suitable excipients, wetting agents, disintegrators, and the like. Specifically, by utilizing a preparation having a disintegration property in the large intestine, said preparation being prepared by filling a mixed solution of a pharmacologically active substance with an absorption enhancing composition into capsules and said capsules being coated with one or more layers, the reduction or loss of availability observed in the conventional preparations for a lower gastrointestinal tract, and the unevenness among individuals can greatly be improved.

EXAMPLE

In the following, the absorption enhancer for the large intestine in the invention is explained in more detail and concretely by examples, comparative examples and test examples. However, the invention is not limited in any way by the following examples.

Examples 1 to 12, Comparative examples 1 to 4

Using TRH-T (protirelin tartarate) as the main pharmaceutical entity, prepared according to Table 1 below was an aqueous solution, or a solution of polyethylene glycol of the average molecular weight in the range of 190 to 630, or glycerin, mixed with pyrothiodecane, sodium caprate, dipotassium glycyrrhizinate or sodium deoxycholate as the absorption enhancer.

TABLE 1

| Formulation No. | TRH-T | Absorption enhancer | Hydrophilic medium |
|---|---|---|---|
| Control | 20 mg/ml | Not added | Water |
| Comparative example 1 | 20 mg/ml | Pyrothiodecane 1%, Cyclodextrin 10% | Water |
| Comparative example 2 | 20 mg/ml | Sodium caprate 1% | Water |
| Comparative example 3 | 20 mg/ml | Sodium caprate 1%, Dipotassium glycyrrhizinate 1% | Water |
| Comparative example 4 | 20 mg/ml | Not added | C |
| Example 1 | 20 mg/ml | Sodium deoxycholate 1% | C |
| Example 2 | 20 mg/ml | Pyrothiodecane 1% | C |
| Example 3 | 20 mg/ml | Sodium deoxycholate 1% | Glycerin |
| Example 4 | 20 mg/ml | Pyrothiodecane 1% | Glycerin |
| Example 5 | 20 mg/ml | Sodium cholate 1% | Glycerin |
| Example 6 | 20 mg/ml | Sodium glycocholate 1% | Glycerin |
| Example 7 | 20 mg/ml | Sodium taurocholate 1% | Glycerin |
| Example 8 | 20 mg/ml | Sodium chenodeoxycholate 1% | Glycerin |
| Example 9 | 20 mg/ml | Sodium caprate 1% | Glycerin |
| Example 10 | 20 mg/ml | Sodium caprylate 1% | Glycerin |
| Example 11 | 20 mg/ml | Sodium capronate 1% | Glycerin |
| Example 12 | 20 mg/ml | Sodium cholate 1% | C |
| Example 13 | 20 mg/ml | Sodium glycocholate 1% | C |
| Example 14 | 20 mg/ml | Sodium taurocholate 1% | C |
| Example 15 | 20 mg/ml | Sodium chenodeoxycholate 1% | C |
| Example 16 | 20 mg/ml | Sodium caprate 1% | C |
| Example 17 | 20 mg/ml | Sodium caprylate 1% | C |
| Example 18 | 20 mg/ml | Sodium capronate 1% | C |
| Example 19 | 20 mg/ml | Pyrothiodecane 1%, Sodium deoxycholate 1% | C |
| Example 20 | 20 mg/ml | Pyrothiodecane 1% | A |
| Example 21 | 20 mg/ml | Pyrothiodecane 1% | B |
| Example 22 | 20 mg/ml | Pyrothiodecane 1% | D |

※A; Polyethylene glycol (the average molecular weight 190–210),
B; Polyethylene glycol (the average molecular weight 285–315),
C; Polyethylene glycol (the average molecular weight 380–420),
D; Polyethylene glycol (the average molecular weight 570–630).

Using each absorption enhancer solution of control, the comparative examples 1 to 4 and the examples 1 to 2, the effect of each absorption enhancer was evaluated by the in situ loop experiment by the rat large intestine. The test was carried out according to the following procedure.

1. After one-week acclimatization, rats fasted for 24 hours were grouped according to the weight.
2. The anesthesia was made by administering intraperitoneally 20% urethane by 5 ml/kg.
3. The jugular vein was exposed by incising the cervical skin.
4. After the abdominal retraction, the large intestine was ligated at the site ca. 5 cm apart from the cecum junction.
5. The drug solution was administered from the upper part of the large intestine, and the administered part was incised.
6. Blood of 500 µl was collected before administration and 15 and 30 minutes, 1, 3 and 6 hours after the administration from the jugular vein, to which an inhibitor solution of 25 µl was added.
7. Centrifugation, 3000 rpm×12 min, was made at 4° C. to recover plasma.
8. TRH in plasma was quantitatively measured by the radioimmunoassay method (RIA method).

The results is as shown in FIG. 1. Comparing the absorption enhancer effect of TRH by each absorption enhancer, the liquid preparation type formulations of sodium deoxycholate+C or pirotiodecane+C showed the strongest absorption enhancer effect (the bioavilability is 52% and 47%, respectively. Then, following was the use of sodium caprate and dipotassium glycyrrhizinate, followed by sodium caprate alone (the bioavilability is 36% and 20% respectively). However, pyrothiodecane alone (2%) resulted in less absorption compared with the control (13%).

From the above results, it has become evident that the extremely high absorption enhancer effect is shown by dissolving pyrothiodecane or sodium deoxycholate in a hydrophilic medium like polyethylene glycol with the average molecular weight in the range of 190 to 630.

INDUSTRIAL APPLICABILITY

The absorption enhancer for the large intestine of the invention makes it possible to greatly increase the absorption enhancer efficiency for physiologically active polypeptides or oligonucleotides administered to the large intestine. Therefore, an oral preparation with a disintegration property in the large intestine, for example, can be obtained by mixing the absorption enhancer for the large intestine of the invention with a pharmacologically active substance, thus the invention having a wide range of use in the pharmaceutical industry.

What is claimed is:

1. An absorption enhancer for the large intestine containing a hydrophilic medium and an absorption enhancer, wherein said absorption enhancer comprises one or more types selected from the group consisting of azacycloalkane derivatives, sodium cholate, sodium glycocholate, sodium taurocholate, sodium chenodeoxycholate and medium-chain fatty acid salts.

2. The absorption enhancer for the large intestine according to claim 1, wherein the hydrophilic medium is polyethylene glycol with an average molecular weight in the range of 190 to 630 or glycerin.

3. The absorption enhancer for the large intestine according to claim 1, wherein the freezing point of the hydrophilic medium is 25° C. or lower.

4. The absorption enhancer for the large intestine according to claim 1, wherein the relative wettability of the hydrophilic medium is 40 to 100.

5. The absorption enhancer for the large intestine according to claim 1, wherein the mixed amount of the hydrophilic medium in the total amount of a preparation is 30 to 90%.

6. The absorption enhancer for the large intestine according to claim 1, wherein the azacycloalkane derivative is 1-[2-(decylthio)ethyl]azacyclopentan-2-one.

7. The absorption enhancer for the large intestine according to claim 1, wherein the medium-chain fatty acid salt is one or more types selected from alkaline metal salts of capric acid, caprylic acid or caproic acid.

8. The absorption enhancer for the large intestine according to claim 1, wherein the mixed amount of the absorption enhancer in the total amount of the preparation is 5 to 50%.

9. The absorption enhancer for the large intestine according to claim 1, wherein the mixing ratio of the absorption enhancer for the hydrophilic medium is 1:1 to 1:100.

10. An oral preparation comprising the absorption enhancer for the large intestine as in any of claims 1–11.

11. The oral preparation of claim 10 further comprising a physiologically active peptide and/or oligonucleotide as an active ingredient.

12. An absorption enhancer with increased absorption enhancer efficiency comprising an absorption enhancer dissolved in a hydrophilic medium, wherein said absorption enhancer comprises one or more types selected from the group consisting of azacycloalkane derivatives, sodium cholate, sodium glycocholate, sodium taurocholate, sodium deoxycholate, sodium chenodeoxycholate and medium-chain fatty acid salts.

13. A method for producing an absorption enhancer with increased absorption enhancer efficiency comprising dissolving an absorption enhancer in a hydrophilic medium.

* * * * *